(12) United States Patent
Mizukami

(10) Patent No.: US 10,548,460 B2
(45) Date of Patent: Feb. 4, 2020

(54) SIGNAL PROCESSING APPARATUS AND MEDICAL OBSERVATION SYSTEM

(71) Applicant: Sony Olympus Medical Solutions Inc., Tokyo (JP)

(72) Inventor: Aki Mizukami, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 15/567,619

(22) PCT Filed: Feb. 22, 2016

(86) PCT No.: PCT/JP2016/055116
§ 371 (c)(1),
(2) Date: Oct. 19, 2017

(87) PCT Pub. No.: WO2016/174903
PCT Pub. Date: Nov. 3, 2016

(65) Prior Publication Data
US 2018/0116486 A1 May 3, 2018

(30) Foreign Application Priority Data
Apr. 30, 2015 (JP) ................. 2015-093677

(51) Int. Cl.
A61B 1/00 (2006.01)
A61B 1/045 (2006.01)
(Continued)

(52) U.S. Cl.
CPC ........ A61B 1/00009 (2013.01); A61B 1/0002 (2013.01); A61B 1/00197 (2013.01);
(Continued)

(58) Field of Classification Search
CPC ............ A61B 1/00009; A61B 1/00006; A61B 1/0002; A61B 1/00197; A61B 1/045; H04N 5/23245
(Continued)

(56) References Cited

U.S. PATENT DOCUMENTS

2002/0105409 A1 8/2002 Nakamitsu et al.
2008/0262306 A1* 10/2008 Kawai ................ A61B 1/00039
600/118
(Continued)

FOREIGN PATENT DOCUMENTS

EP 1 972 257 A1 9/2008
EP 1 972 258 A1 9/2008
(Continued)

OTHER PUBLICATIONS

International Search Report dated May 24, 2016 in PCT/JP2016/055116 filed Feb. 22, 2016.
(Continued)

Primary Examiner — Nguyen T Truong
(74) Attorney, Agent, or Firm — Xsensus LLP

(57) ABSTRACT

A signal processing apparatus 6 includes a mode selection unit 6124 that selects any operational mode from among a plurality of operational modes that include a regular operational mode in which a video signal for display is output, and are hierarchically organized in a tree form, the mode selection unit 6124 causing the signal processing apparatus 6 to operate in the selected operational mode. The operational modes include a plurality of lower-level operational modes as lower-level operational modes having a parent-child relation with the regular operational mode. The mode selection unit 6124, after the signal processing apparatus 6 has started up, selects any operational mode from among same-level operational modes for each level from an upper level
(Continued)

toward a lower level and, when having selected any of the lower-level operational modes, can select an upper-level operational mode relative to the selected lower-level operational mode on condition that the signal processing apparatus 6 has again started up.

12 Claims, 5 Drawing Sheets

(51) Int. Cl.
*H04N 5/232* (2006.01)
*H04N 5/225* (2006.01)

(52) U.S. Cl.
CPC ......... *A61B 1/045* (2013.01); *H04N 5/23245* (2013.01); *H04N 2005/2255* (2013.01)

(58) Field of Classification Search
USPC .......................................................... 348/65
See application file for complete search history.

(56) References Cited

U.S. PATENT DOCUMENTS

| | | | |
|---|---|---|---|
| 2008/0262310 A1 | 10/2008 | Kawai | |
| 2009/0244273 A1 | 10/2009 | Usami | |
| 2013/0300836 A1 | 11/2013 | Zhao et al. | |
| 2013/0300837 A1 | 11/2013 | Dicarlo et al. | |
| 2014/0340496 A1 | 11/2014 | Okawa et al. | |
| 2016/0227129 A1 | 8/2016 | Zhao et al. | |
| 2018/0249089 A1 | 8/2018 | Zhao et al. | |

FOREIGN PATENT DOCUMENTS

| | | |
|---|---|---|
| JP | 2000-175544 A | 6/2000 |
| JP | 2001-184166 A | 7/2001 |
| JP | 2001-256711 A | 9/2001 |
| JP | 2007-185355 A | 7/2007 |
| JP | 2007-185356 A | 7/2007 |
| JP | 2009-195621 A | 9/2009 |
| JP | 2009-226169 A | 10/2009 |
| JP | 2009-226170 A | 10/2009 |
| JP | 2010-4979 A | 1/2010 |

OTHER PUBLICATIONS

Combined Chinese Office Action and Search Report dated Jan. 28, 2019 in corresponding Chinese Patent Application No. 201680023392.0 (with English Translation), 13 pages.
Extended European Search Report dated Oct. 9, 2018 in corresponding European Patent Application No. 16786180.6, 7 pages.
Japanese Office Action dated Sep. 3, 2019 in Japanese Patent Application No. 2017-515406.

* cited by examiner

SIGNAL PROCESSING APPARATUS AND MEDICAL OBSERVATION SYSTEM

FIELD

The present invention relates to a signal processing apparatus that processes an image signal output from a medical observation apparatus such as an endoscope and a medical observation system including the signal processing apparatus.

BACKGROUND

A medical observation system that images the inside of a subject such as a human (the inside of a living body) using an imaging element to observe the inside of a living body is conventionally known in the field of medicine (refer to Patent Literature 1, for example).

The medical observation system (an electrically bending endoscope apparatus) described in Patent Literature 1 includes an endoscope (an electrically bending endoscope) that images the inside of a living body, a signal processing apparatus (an image processing apparatus) that processes an imaging signal from the endoscope, and a display apparatus (a monitor) that displays a taken image based on a video signal processed by the signal processing apparatus.

The medical observation system described in Patent Literature 1 includes a plurality of operational modes (a running mode, a maintenance mode, a calibration mode, an abnormal stop mode, and the like) and can be operated on any operational mode among the operational modes.

CITATION LIST

Patent Literature

Patent Literature 1: Japanese Patent Application Laid-open No. 2007-185356

SUMMARY

Technical Problem

In the medical observation system described in Patent Literature 1, when a regular operational mode that displays a taken image based on the imaging signal from the endoscope is set as the operational mode, for example, the following problem arises.

When switching the operational modes, the medical observation system described in Patent Literature 1 can switch to any operational mode among the operational modes. For this reason, even when the medical observation system is operating on the regular operational mode (while a taken image and the like are being displayed), for example, the medical observation system can switch also to any mode that does not display the taken image and the like (the maintenance mode, for example) through operation by an operator or the like. In other words, the problem is that when an operational error by the operator or the like occurs while the taken image and the like are being displayed, the medical observation system switches to an unintentional operational mode, and the display becomes lost in the midst of operation (hereinafter, referred to as image loss).

Given these circumstances, demanded is a technique that can avoid switching to the unintentional operational mode to prevent image loss.

The present invention has been made in view of the foregoing, and an object thereof is to provide a signal processing apparatus and a medical observation system that can avoid switching to an unintentional operational mode to prevent image loss.

Solution to Problem

To solve the above-described problem and achieve the object, a signal processing apparatus according to the present invention is connected to a medical observation apparatus that examines an inside of a subject and outputs an image signal responsive to an examination result and performs image processing on the image signal, and includes a mode selection unit configured to select any operational mode from among a plurality of operational modes that include a regular operational mode in which a video signal for display is output, the operational modes being hierarchically organized in a tree form, the mode selection unit causing the signal processing apparatus to operate in the selected operational mode, wherein the operational modes includes a plurality of lower-level operational modes as lower-level operational modes having a parent-child relation with the regular operational mode, and the mode selection unit, after the signal processing apparatus has started up, selects any operational mode from among same-level operational modes for each level from an upper level toward a lower level and, when having selected any of the lower-level operational modes, is capable of selecting an upper-level operational mode relative to the selected lower-level operational mode on condition that the signal processing apparatus has again started up.

In the above-described invention, the signal processing apparatus includes a first image processor configured to perform first image processing on the image signal, the lower-level operational modes include a normal mode in which the first image processor is caused to execute the first image processing to output a first video signal for display and an abnormal mode in which a second video signal for display different from the first video signal is output, and the mode selection unit selects the regular operational mode, then determines a state of the first video signal, and selects the normal mode or the abnormal mode based on a determination result.

In the above-described invention, the signal processing apparatus includes a second image processor configured apart from the first image processor and configured to perform second image processing different from the first image processing on the image signal, the operational modes include a simple image output mode in which the second image processor is caused to perform the second image processing to output a third video signal for display, and a fixed image output mode in which a fourth video signal for display responsive is output to a preset fixed image as lower-level operational modes having a parent-child relation with the abnormal mode, and the mode selection unit selects the abnormal mode, then determines a state of the third video signal, and selects the simple image output mode or the fixed image output mode based on a determination result.

In the above-described invention, in the signal processing apparatus, the second image processor includes a programmable logic device.

In the above-described invention, in the signal processing apparatus, the operational modes include a maintenance mode for maintenance of the signal processing apparatus as an operational mode on a same level as the regular operational mode.

In the above-described invention, in the signal processing apparatus, the regular operational mode and the maintenance mode are top-level operational modes among the operational modes.

In the above-described invention, in the signal processing apparatus, when having selected the maintenance mode, the mode selection unit enables the regular operational mode to be selected on condition that the signal processing apparatus has again started up.

A medical observation system according to the present invention includes: a medical observation apparatus that examines an inside of a subject and outputs an image signal responsive to an examination result; and the above-described signal processing apparatus.

Advantageous Effects of Invention

In the signal processing apparatus according to the present embodiment, the operational modes are hierarchically organized in a tree form. The signal processing apparatus, after the start-up of the signal processing apparatus, selects any operational mode from among same-level operational modes for each level from an upper level toward a lower level and switches to the operational mode. When having switched to a lower-level operational mode (a lower-level operational mode having a parent-child relation with the regular operational mode), the signal processing apparatus can switch to an upper-level operational mode relative to the lower-level operational mode on condition that the signal processing apparatus has again started up.

Consequently, the signal processing apparatus according to the present embodiment produces an effect of making it possible to, when once having switched to the lower-level operational mode, avoid switching to an unintentional operational mode (the maintenance mode, for example) and to prevent image loss even when an operational error by an operator or the like occurs.

The medical observation system according to the present invention includes the signal processing apparatus and thus produces an effect similar to that of the signal processing apparatus.

DESCRIPTION OF EMBODIMENTS

Figure 1:
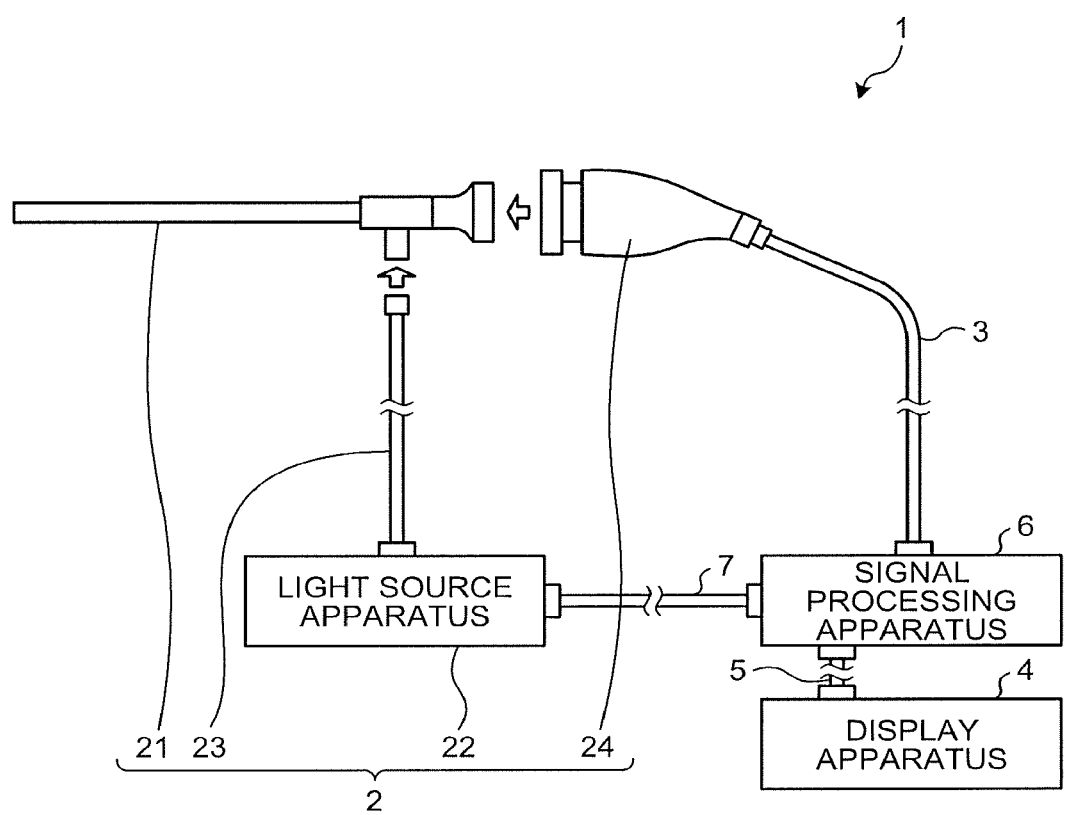
FIG. 1 is a diagram of a schematic configuration of a medical observation system according to an embodiment of the present invention.

The following describes an embodiment for performing the present invention (hereinafter, an embodiment) with reference to the accompanying drawings. The embodiment described below does not limit the present invention. Further, in the drawings, the same components are denoted by the same symbols.

Schematic Configuration of Medical Observation System

FIG. 1 is a diagram of a schematic configuration of a medical observation system 1 according to the embodiment of the present invention.

The medical observation system 1 is a system that is used in the field of medicine and observes the inside of a subject such as a human (the inside of a living body). As illustrated in FIG. 1, this medical observation system 1 includes an endoscope 2, a first transmission cable 3, a display apparatus 4, a second transmission cable 5, a signal processing apparatus 6, and a third transmission cable 7.

The endoscope 2 has a function as a medical observation apparatus according to the present invention, examines the inside of a living body, and outputs a signal responsive to an examination result. As illustrated in FIG. 1, this endoscope 2 includes an insertion unit 21, a light source apparatus 22, a light guide 23, and a camera head 24.

The insertion unit 21 is hard, has an elongated shape, and is inserted into the inside of a living body. This insertion unit 21 incorporates an optical system that includes one or more lenses and collects a subject image.

The light source apparatus 22, to which one end of the light guide 23 is connected, supplies light for illuminating the inside of a living body to the one end of the light guide 23 under the control by the signal processing apparatus 6.

The one end of the light guide 23 is detachably connected to the light source apparatus 22, and the other end thereof is detachably connected to the insertion unit 21. The light guide 23 transmits the light supplied from the light source apparatus 22 from the one end to the other end and supplies the light to the insertion unit 21. The light supplied to the insertion unit 21 is emitted from a tip of the insertion unit 21 to be applied to the inside of a living body. The light applied to the inside of a living body (the subject image) is collected by the optical system within the insertion unit 21.

The camera head 24 is detachably connected to a basal end of the insertion unit 21. The camera head 24 takes the subject image collected by the insertion unit 21 and outputs an imaging signal caused by the imaging (corresponding to an image signal responsive to an examination result according to the present invention) under the control by the signal processing apparatus 6.

In the present embodiment, the camera head 24 photoelectrically converts the imaging signal into an optical signal and outputs the imaging signal as the optical signal.

One end of the first transmission cable 3 is detachably connected to the signal processing apparatus 6, and the other end thereof is detachably connected to the camera head 24. Specifically, the first transmission cable 3 is a cable that arranges a plurality of electric wires (not illustrated) and optical fibers (not illustrated) inside a sheath as an outermost layer.

The electric wires are electric wires for transmitting a control signal, a sync signal, a clock, electric power, and the like output from the signal processing apparatus 6 to the camera head 24.

The optical fibers are optical fibers for transmitting the imaging signal (the optical signal) output from the camera head 24 to the signal processing apparatus 6. When the imaging signal is output from the camera head 24 as an electric signal, the optical fibers may be changed to electric wires.

The display apparatus 4 (a monitor with SD, HD, 4K or more, for example) displays images under the control by the signal processing apparatus 6.

One end of the second transmission cable 5 (HD-SDI or 3G-SDI, HDMI (registered trademark), or DisplayPort (registered trademark), for example) is detachably connected to the display apparatus 4, and the other end thereof is detachably connected to the signal processing apparatus 6. The second transmission cable 5 transmits a video signal processed by the signal processing apparatus 6 to the display apparatus 4.

The signal processing apparatus 6 includes a CPU and comprehensively controls the operation of the light source apparatus 22, the camera head 24, and the display apparatus 4.

One end of the third transmission cable 7 is detachably connected to the light source apparatus 22, and the other end thereof is detachably connected to the signal processing apparatus 6. The third transmission cable 7 transmits the control signal from the signal processing apparatus 6 to the light source apparatus 22.

Configuration of Signal Processing Apparatus

The following describes a configuration of the signal processing apparatus 6.

The following mainly describes a function of processing the imaging signal input from the camera head 24 via the first transmission cable 3 as the signal processing apparatus 6.

Figure 2:
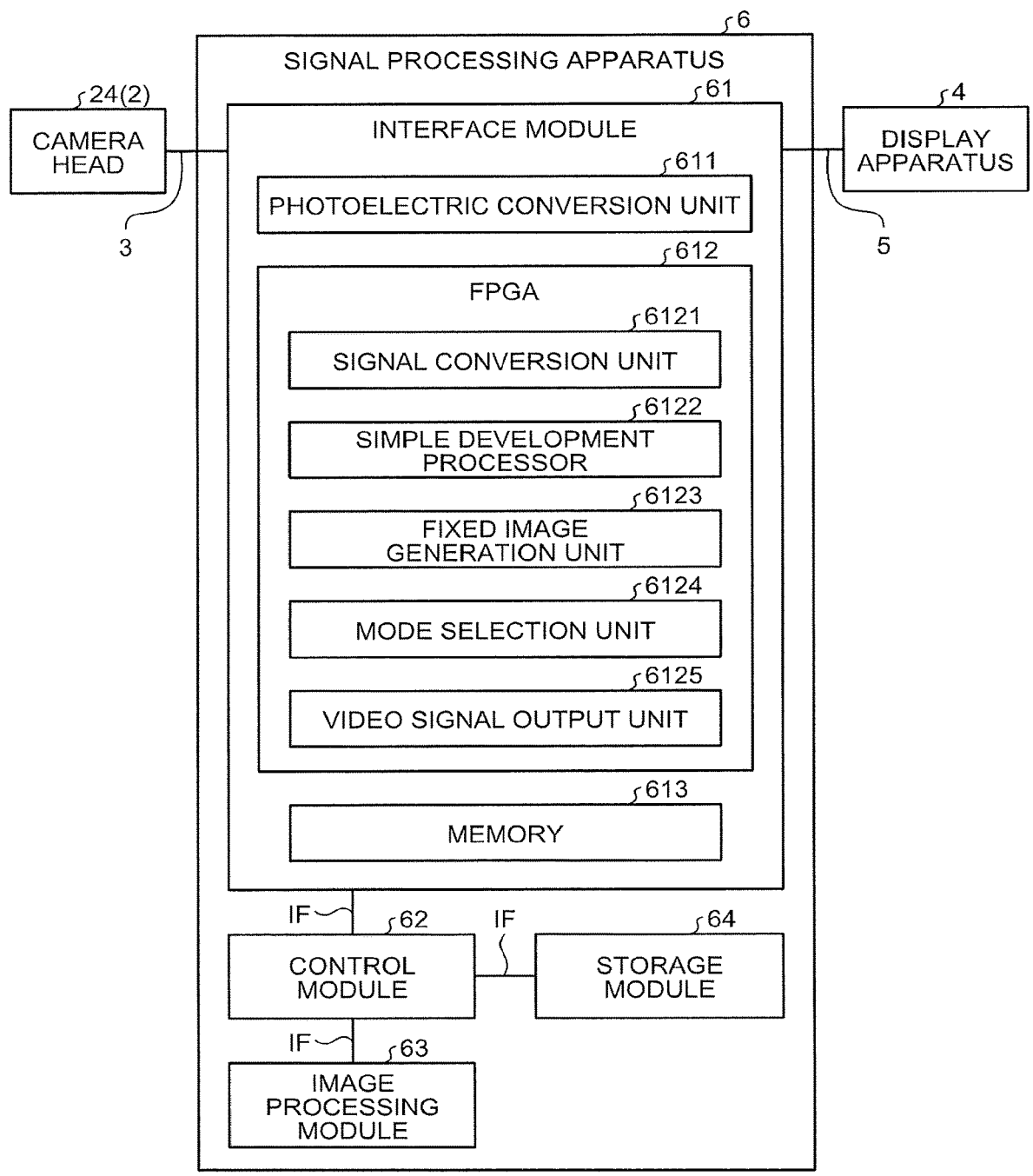
FIG. 2 is a block diagram of a configuration of the signal processing apparatus illustrated in FIG. 1.

FIG. 2 is a block diagram of the configuration of the signal processing apparatus 6.

FIG. 2 omits the illustration of a connector that causes the camera head 24 and the first transmission cable 3 to be detachable, a connector that causes the first transmission cable 3 and the signal processing apparatus 6 to be detachable, a connector that causes the display apparatus 4 and the second transmission cable 5 to be detachable, and a connector that causes the second transmission cable 5 and the signal processing apparatus 6 to be detachable. FIG. 2 illustrates the electric wires and the optical fibers included in the first transmission cable 3 as one cable.

The signal processing apparatus 6 is assembled using a general-purpose PC architecture.

Specifically, as illustrated in FIG. 2, the signal processing apparatus 6 includes an interface module 61, a control module 62, an image processing module 63, and a storage module 64 that are connected to each other using general-purpose interfaces IF.

Although specific illustration is omitted, the modules 61 to 64 are arranged within respective casings. The signal processing apparatus 6 is assembled, tested and the like, and is then set to be a state in which the inside of the casings is unable to be open.

The interfaces IF are interfaces having a communication protocol and a connector shape compliant with an interface standard for communication (the PC/AT compatible machine standard, for example).

The present embodiment employs PCI Express (PCIe (registered trademark)) as the interfaces IF. In other words, in the present embodiment, the modules 62 to 64 include respective PC parts compliant with the PCIe standard.

The control module 62 controls the operation of the light source apparatus 22, the operation of the camera head 24, the operation of the display apparatus 4, and the operation of the entire signal processing apparatus 6.

In the present embodiment, the control module 62 includes a mother board compliant with the standard of the PC/AT compatible machine with a CPU and the like mounted. The mother board includes respective expansion slots to be connected to the interface module 61, the image processing module 63, and the storage module 64.

The interface module 61 is mounted on the expansion slot provided in the control module 62 (the PCIe slot in the present embodiment). As illustrated in FIG. 2, this interface module 61 includes a photoelectric conversion unit 611, a field programmable gate array (FPGA) 612, and a memory 613.

The photoelectric conversion unit 611 photoelectrically converts the imaging signal (the optical signal) input from the camera head 24 via the first transmission cable 3 into an electric signal and outputs the photoelectrically converted imaging signal to the FPGA 612. When the imaging signal is output from the camera head 24 as the electric signal, the photoelectric conversion unit 611 is omitted, and the electric signal is directly input to the FPGA 612.

The FPGA 612 is a logic circuit configured by the control module 62. As illustrated in FIG. 2, this FPGA 612 includes a signal conversion unit 6121, a simple development processor 6122, a fixed image generation unit 6123, a mode selection unit 6124, and a video signal output unit 6125.

The signal conversion unit 6121 converts the imaging signal photoelectrically converted by the photoelectric conversion unit 611 into a digital signal conforming to the interface standard for communication (the PCIe standard in the present embodiment). The converted digital signal is once stored in a memory (not illustrated) such as a video random access memory (VRAM) and is then output to the control module 62 via the interface IF.

The simple development processor 6122 has a function as a second image processor according to the present invention and performs various kinds of image processing (image processing simpler (lower in processing load) than image processing by the image processing module 63 (corresponding to second image processing according to the present invention)) on the digital signal stored in the memory (not illustrated) such as a VRAM to generate a third video signal. The simple development processor 6122 then outputs the third video signal to the video signal output unit 6125.

The fixed image generation unit 6123 generates a fourth video signal based on a preset fixed image such as a test pattern. The fixed image generation unit 6123 then outputs the fourth video signal to the video signal output unit 6125.

The mode selection unit 6124 selects any operational mode from among the operational modes and causes the signal processing apparatus 6 to operate on the selected operational mode.

The operational modes are hierarchically organized in a tree form as described below.

Figure 3:
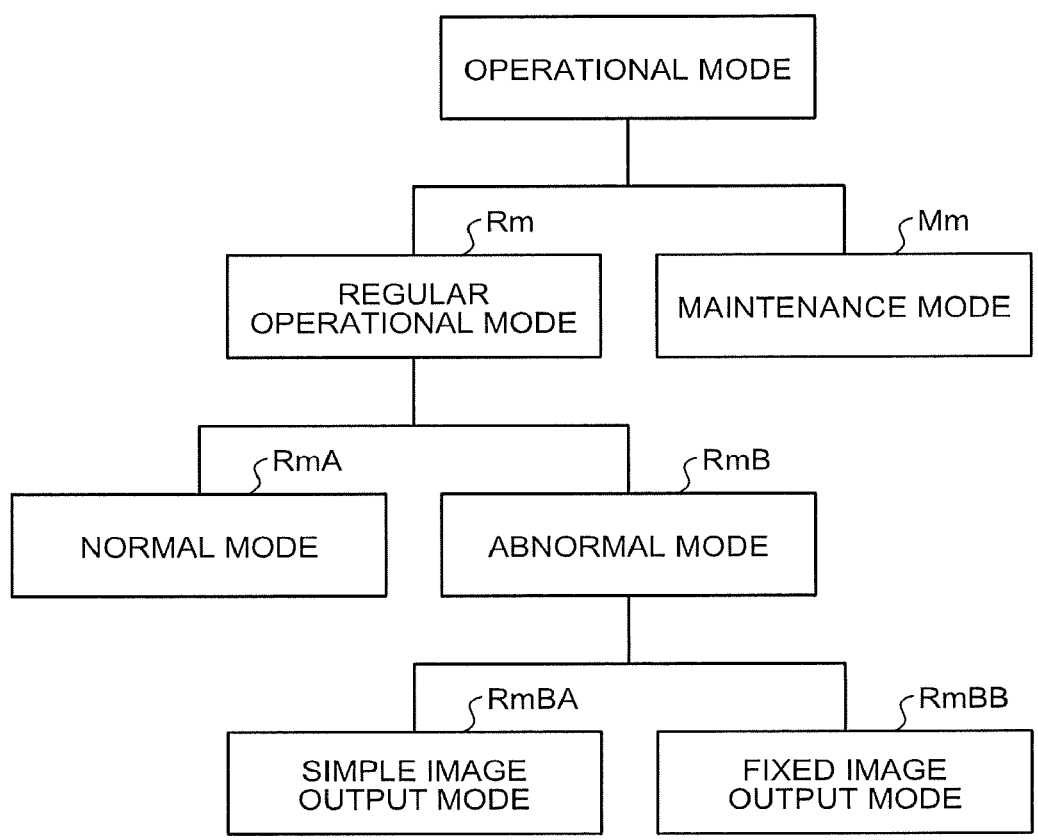
FIG. 3 is a diagram of a hierarchical structure of operational modes to be selected by the mode selection unit illustrated in FIG. 2.

FIG. 3 is a diagram of a hierarchical structure of the operational modes to be selected by the mode selection unit 6124.

As illustrated in FIG. 3, the operational modes include a maintenance mode Mm, a regular operational mode Rm, a normal mode RmA, an abnormal mode RmB, a simple image output mode RmBA, and a fixed image output mode RmBB.

As illustrated in FIG. 3, the maintenance mode Mm and the regular operational mode Rm are same-level operational modes and are top-level operational modes among the operational modes.

Specifically, the maintenance mode Mm is an operational mode for maintenance for upgrading part of the functions of the interface module 61 and the like.

The regular operational mode Rm is an operational mode in which a video signal (a first video signal or a second video signal) is output to the display apparatus 4 via the second transmission cable 5 and the display apparatus 4 is caused to display an image based on the video signal.

The normal mode RmA and the abnormal mode RmB are operational modes corresponding to lower-level operational modes according to the present invention and are operational modes that have a parent-child relation with the regular operational mode Rm and are on a level below the regular operational mode Rm as illustrated in FIG. 3.

Specifically, the normal mode RmA is an operational mode in which the first video signal generated by the image processing by the image processing module 63 (corresponding to first image processing according to the present invention) is output to the display apparatus 4 and the display apparatus 4 is caused to display an image based on the first video signal (hereinafter, referred to as a regular image).

The abnormal mode RmB is an operational mode in which the second video signal different from the first video signal (the third video signal or the fourth video signal) is output to the display apparatus 4 and the display apparatus 4 is caused to display an image based on the second video signal.

As illustrated in FIG. 3, the simple image output mode RmBA and the fixed image output mode RmBB are operational modes that have a parent-child relation with the abnormal mode RmB and are on a level below the abnormal mode RmB.

Specifically, the simple image output mode RmBA is an operational mode in which the third video signal generated by the image processing by the simple development processor 6122 is output to the display apparatus 4 and the display apparatus 4 is caused to display an image based on the third video signal (hereinafter, referred to as a simple image).

The fixed image output mode RmBB is an operational mode in which the fourth video signal generated by the fixed image generation unit 6123 is output to the display apparatus 4 and the display apparatus 4 is caused to display an image based on the fourth video signal (the fixed image such as a test pattern).

The mode selection unit 6124, after the start-up of the medical observation system 1 (after the power is turned on), selects any operational mode from among same-level operational modes for each level from an upper level toward a lower level as will be specifically described below.

The video signal output unit 6125 selects any video signal from among the first video signal (the video signal generated by the image processing module 63 and input via the interface IF and the control module 62), the third video signal (the video signal generated by the simple development processor 6122), and the fourth video signal (the video signal generated by the fixed image generation unit 6123) in accordance with the operational mode selected by the mode selection unit 6124 and outputs the selected video signal to the display apparatus 4 via the second transmission cable 5.

In this process, the video signal output unit 6125 receives input of an instruction to select any video signal out of the first, the third, and the fourth video signals and setting information on a video format such as image size corresponding to the selected operational mode (the normal mode RmA, the simple image output mode RmBA, or the fixed image output mode RmBB) from the mode selection unit 6124. The video signal output unit 6125 then converts the image size and the like of the selected video signal based on the setting information and outputs the converted video signal to the display apparatus 4 via the second transmission cable 5.

The memory 613 includes a non-volatile memory and stores therein mode shift information used in the selection of the maintenance mode Mm or the regular operational mode Rm by the mode selection unit 6124 and the setting information on the video format such as image size corresponding to the operational mode (the normal mode RmA, the simple image output mode RmBA, or the fixed image output mode RmBB).

The image processing module 63 includes a general-purpose computing on graphics processing unit (GPGPU), for example, and is mounted on the expansion slot provided in the control module 62 (the PCIe slot in the present embodiment).

Specifically, the image processing module 63 performs various kinds of image processing such as development processing, noise reduction, color correction, color enhancement, and contour enhancement (corresponding to the first image processing according to the present invention) on the digital signal (the imaging signal) output from the interface module 61 and input via the interface IF and the control module 62 to generate the first video signal. The image processing module 63 then outputs the first video signal to the control module 62 via the interface IF.

The storage module 64 includes a solid state drive (SSD), a hard disk drive (HDD), or a dual inline memory module (DIMM), for example, and is mounted on the expansion slot provided in the control module 62 (an IDE/SATA connector and a memory socket in the present embodiment).

Specifically, the storage module 64 houses a computer program and an OS (Windows (registered trademark), Linux (registered trademark), Android (registered trademark), iOS (registered trademark), or RTOS, for example) that causes the image processing module 63 to execute the various kinds of image processing.

Operation of Signal Processing Apparatus

The following describes the operation of the signal processing apparatus 6.

Figure 4:
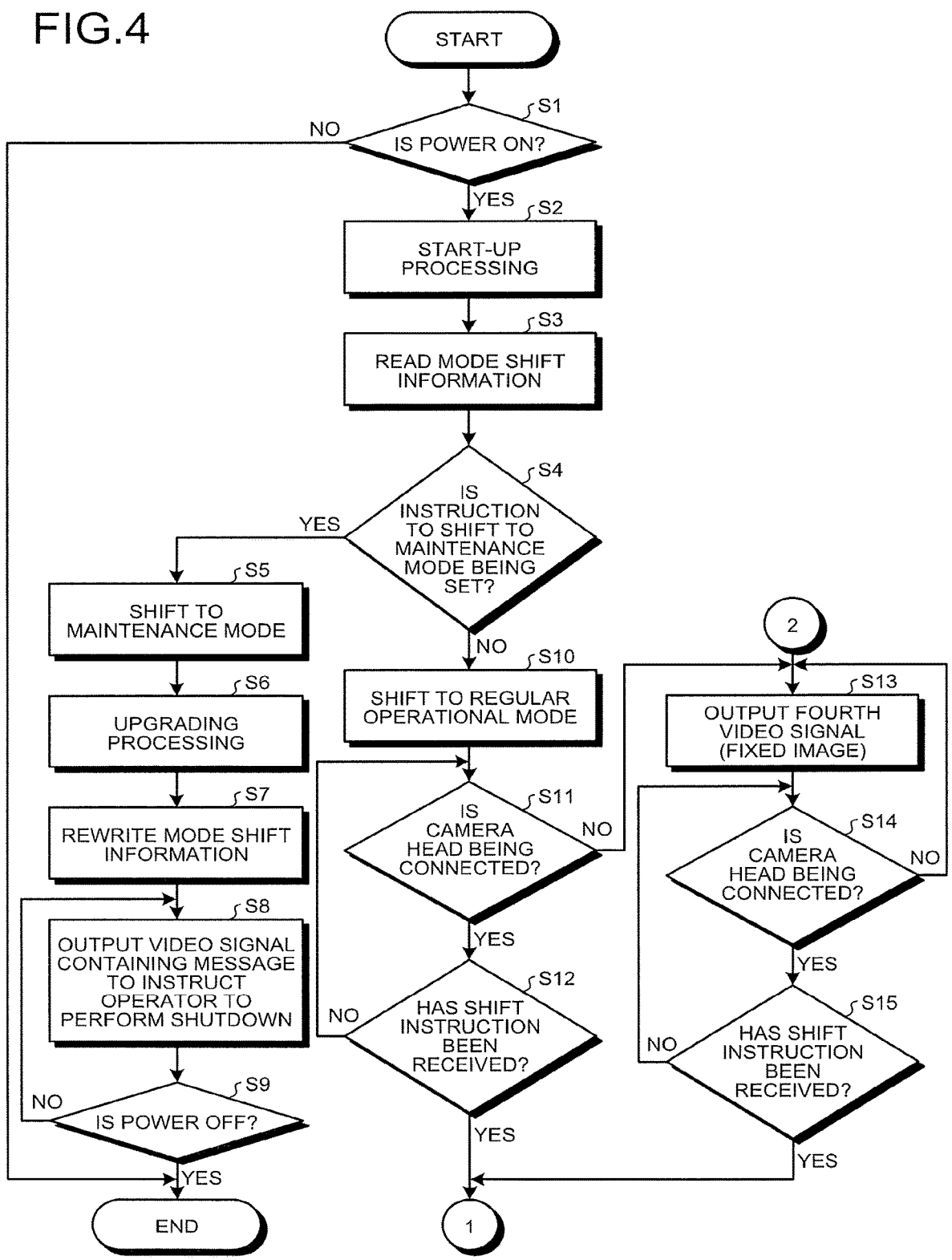
FIG. 4 is a flowchart of the operation of the signal processing apparatus illustrated in FIG. 1.
Figure 5:
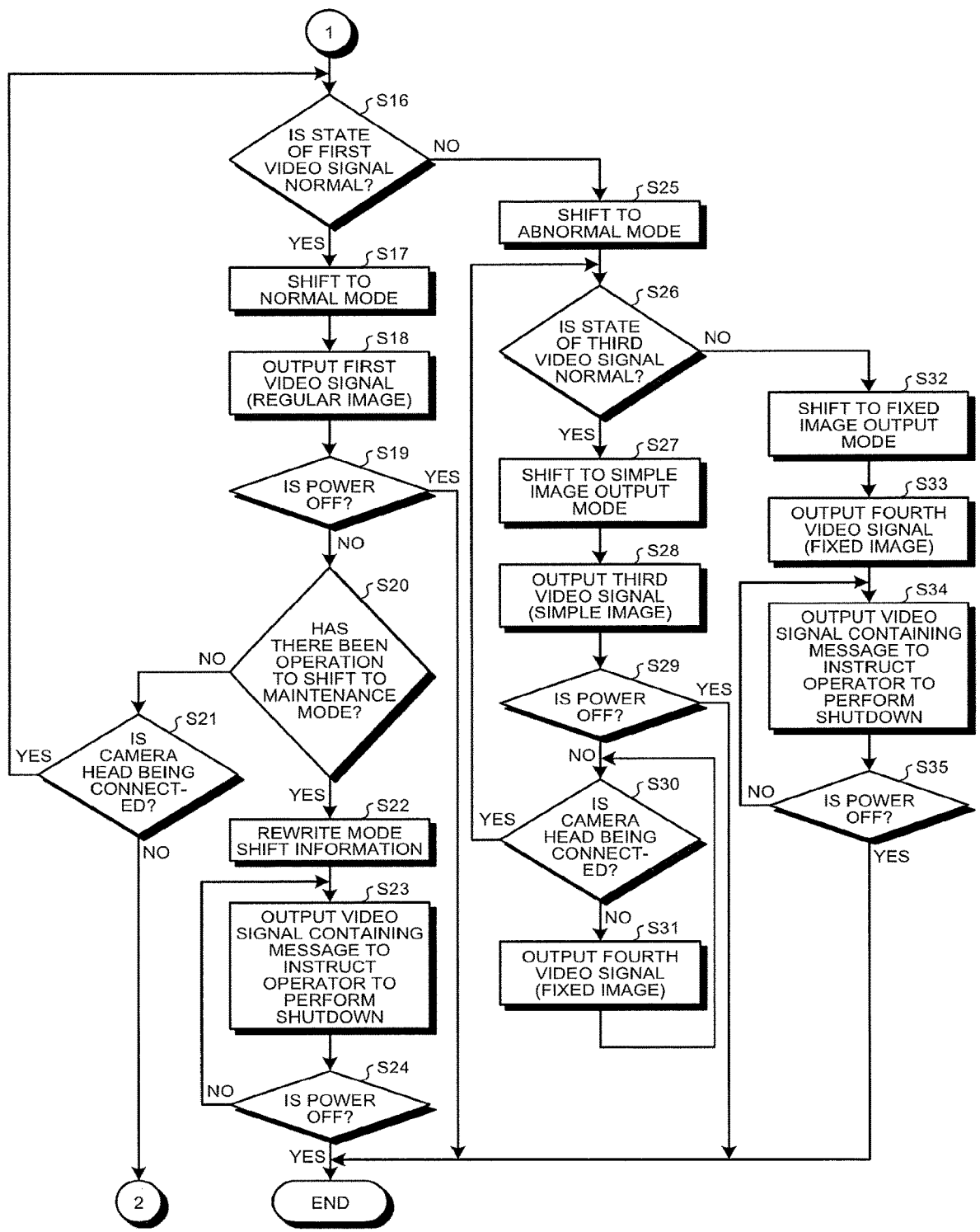
FIG. 5 is a flowchart of the operation of the signal processing apparatus illustrated in FIG. 1.

FIG. 4 and FIG. 5 are flowchart of the operation of the signal processing apparatus 6.

If the power is turned on (Yes at Step S1), the signal processing apparatus 6, the camera head 24, and the like execute start-up processing in accordance with the power-on (Step S2).

After the start-up of the interface module 61 (Step S2), the mode selection unit 6124 reads mode shift information from the memory 613 (Step S3). The mode selection unit 6124 then determines whether an instruction to shift to the "maintenance mode Mm" is being set in the read mode shift information (Step S4).

If it is determined that the instruction to shift to the "maintenance mode Mm" is being set in the mode shift information (Yes at Step S4), the mode selection unit 6124 provides notification that the signal processing apparatus 6 will be shifted to the maintenance mode Mm to the control module 62 and peripheral devices such as the camera head 24 and shifts the signal processing apparatus 6 to the maintenance mode (Step S5).

After Step S5, the control module 62 reads upgrading data for upgrading part of the functions of the interface module 61 and the like from a USB memory (not illustrated), for example, mounted on the control module 62. In addition, the control module 62 transfers the upgrading data to the interface module 61 via the interface IF. The interface module 61 executes upgrading processing to upgrade part of the functions based on the upgrading data (Step S6).

After Step S6, the control module 62 rewrites the mode shift information stored in the memory 613 via the interface IF to set an instruction to shift to the "regular operational mode Rm" in the mode shift information (Step S7).

After Step S7, the control module 62 controls the operation of the interface module 61 via the interface IF to cause the interface module 61 to output a certain video signal (a shutdown instruction image containing a message to instruct an operator to perform shutdown (power-off) (a message such as "Turn off power.") (Step S8). With this processing, the display apparatus 4 receives input of the video signal via the second transmission cable 5 and displays the shutdown instruction image based on the video signal.

If the power is turned off (Yes at Step S9), the signal processing apparatus 6 ends this processing. In contrast, if the power-on state is maintained (No at Step S9), the signal processing apparatus 6 returns to Step S8. In other words, the display of the shutdown instruction image continues until the power is turned off.

As described above, in the present embodiment, when once having switched to the maintenance mode Mm, the signal processing apparatus 6 is unable to switch to the regular operational mode Rm unless the signal processing apparatus 6 again starts up.

If it is determined that an instruction to shift to the "regular operational mode Rm" is being set in the mode shift information at Step S4 (No at step S4), the mode selection unit 6124 provides notification that the signal processing apparatus 6 will be shifted to the regular operational mode Rm to the control module 62 and the peripheral devices such as the camera head 24 and shifts the signal processing apparatus 6 to the regular operational mode Rm (Step S10).

After Step S10, the mode selection unit 6124 determines whether the camera head 24 is being connected to the signal processing apparatus 6 via the first transmission cable 3 (Step S11).

The mode selection unit 6124 determines that the camera head 24 is being connected if the imaging signal (the optical signal) is being input from the camera head 24 via the first transmission cable 3 at step S11, for example. If the imaging signal (the optical signal) is not being input, the mode selection unit 6124 determines that the camera head 24 is not being connected.

If it is determined that the camera head 24 is being connected (Yes at Step S11), the mode selection unit 6124 determines whether an instruction to shift to the normal mode RmA or the abnormal mode RmB has been received from the control module 62 via the interface IF (Step S12).

If it is determined that the shift instruction has not been received (No at Step S12), the signal processing apparatus 6 returns to Step S11. In other words, the mode selection unit 6124 continues to monitor the connected state of the camera head 24 until the shift instruction is received.

In contrast, if it is determined that the shift instruction has been received (Yes at Step S12), the signal processing apparatus 6 shifts to Step S16.

If it is determined that the camera head 24 is not being connected at Step S11 (No at Step S11), the mode selection unit 6124 outputs an instruction to select the fourth video signal (the video signal generated by the fixed image generation unit 6123) to the video signal output unit 6125. The video signal output unit 6125 then selects the fourth video signal and outputs the fourth video signal to the display apparatus 4 via the second transmission cable 5 (Step S13). With this processing, the display apparatus 4 displays the fixed image based on the fourth video signal.

After Step S13, the mode selection unit 6124 determines whether the camera head 24 is being connected similarly to Step S11 (Step S14).

If it is determined that the camera head 24 is not being connected (No at Step S14), the signal processing apparatus 6 returns to Step S13. In other words, the display of the fixed image continues until the camera head 24 is connected.

In contrast, if it is determined that the camera head 24 is being connected (Yes at Step S14), the mode selection unit 6124 determines whether the shift instruction has been received from the control module 62 similarly to Step S12 (Step S15).

If it is determined that the shift instruction has not been received (No at Step S15), the signal processing apparatus 6 returns to Step S14. In other words, the mode selection unit 6124 continues to monitor the connected state of the camera head 24 until the shift instruction is received.

In contrast, if it is determined that the shift instruction has been received (Yes at Step S15), the signal processing apparatus 6 shifts to Step S16.

If it is determined that the shift instruction has been received (Yes at Step S12, Yes at Step S15), the mode selection unit 6124 determines the state of the first video signal generated by the image processing module 63 and input via the interface IF and the control module 62 to determine whether the state of the first video signal is normal (Step S16).

The mode selection unit 6124 determines the state of the first video signal based on a frame ID attached to the first video signal as described below at Step S16, for example.

In other words, the camera head 24 outputs an imaging signal (an optical signal) in which a frame ID (hereinafter, referred to as a first frame ID) is attached to each frame so as to be consecutive in a time series order to the signal processing apparatus 6 via the first transmission cable 3. The control module 62 copies the first frame ID attached by the camera head 24 for each frame to the first video signal generated by the image processing module 63 and again attaches a frame ID (hereinafter, referred to as a second frame ID) to each frame.

The mode selection unit 6124 checks the first and second frame IDs contained in the input first video signal and determines whether the first frame ID and the second frame ID match for each frame and whether the first frame ID (the second frame ID also) is consecutive among the frames. If the first frame ID and the second frame ID match for each frame and if the first frame ID (the second frame ID also) is consecutive among the frames, the mode selection unit 6124 determines the state of the first video signal to be normal. In contrast, if the first frame ID and the second frame ID do not match for each frame or if the first frame ID (the second frame ID also) is not consecutive among the frames, the mode selection unit 6124 determines the state of the first video signal to be abnormal (a malfunction has occurred in the image processing module 63 and/or the control module 62, for example).

If it is determined that the state of the first video signal is normal (Yes at Step S16), the mode selection unit 6124 shifts the signal processing apparatus 6 to the normal mode RmA (Step S17). In other words, the mode selection unit 6124 outputs an instruction to select the first video signal and the setting information on the video format such as image size corresponding to the normal mode RmA to the video signal output unit 6125.

After Step S17, the video signal output unit 6125 selects the first video signal from among the first, the third, and the fourth video signals, converts the selected first video signal as appropriate based on the setting information, and outputs the first video signal to the display apparatus 4 via the second transmission cable 5 (Step S18). With this processing, the display apparatus 4 displays the regular image based on the first video signal.

After Step S18, if the power is turned off while the first video signal is being output (Yes at Step S19), the signal processing apparatus 6 ends this processing.

In contrast, if the power-on state is maintained (No at Step S19), the control module 62 determines whether there has been an operation to shift to the maintenance mode Mm (Step S20).

The control module 62 determines whether there has been an operation to shift to the maintenance mode Mm on a menu screen displayed on the display apparatus 4 through operation on an operating unit (not illustrated) such as a mouse, a keyboard, or a touch panel connected to the control module 62 at Step S20, for example.

If it is determined that there has not been any operation to shift to the maintenance mode Mm (No Step at S20), the mode selection unit 6124 determines whether the camera head 24 is being connected similarly to Steps S11 and S14 (Step S21).

If it is determined that the camera head 24 is not being connected (No at Step S21), the signal processing apparatus 6 shifts to Step S13 to execute the output of the fourth video signal (the display of the fixed image).

In contrast, if it is determined that the camera head 24 is being connected (Yes at Step S21), the signal processing apparatus 6 returns to Step S16. In other words, if the power-on state is maintained, there has not been any operation to shift to the maintenance mode Mm, and the connected state of the camera head 24 is maintained while the first video signal is being output, the signal processing apparatus 6 monitors the state of the first video signal on a certain cycle.

If it is determined that there has been an operation to shift to the maintenance mode Mm at Step S20 (Yes at step S20), the control module 62 rewrites the mode shift information stored in the memory 613 via the interface IF to set an instruction to shift to the "maintenance mode Mm" in the mode shift information (Step S22).

After Step S22, the control module 62 causes the interface module 61 to output the certain video signal (the shutdown instruction image) similarly to Step S8 (Step S23). With this processing, the display apparatus 4 receives input of the video signal via the second transmission cable 5 and displays the shutdown instruction image based on the video signal.

If the power is turned off (Yes at Step S24), the signal processing apparatus 6 ends this processing. In contrast, if the power-on state is maintained (No at Step S24), the signal processing apparatus 6 returns to Step S23. In other words, the display of the shutdown instruction image continues until the power is turned off.

As described above, in the present embodiment, when once having switched to the normal mode RmA, the signal processing apparatus 6 is unable to switch to the maintenance mode Mm unless the signal processing apparatus 6 again starts up.

If it is determined that the state of the first video signal is not normal at Step S16 (No at Step S16), the mode selection unit 6124 shifts the signal processing apparatus 6 to the abnormal mode RmB (Step S25). After the shift to the abnormal mode RmB, it is estimated that any malfunction has occurred in the control module 62 and/or the image processing module 63, and the following processing is executed mainly by the interface module 61.

After Step S25, the mode selection unit 6124 determines the state of the third video signal to determine whether the state of the third video signal is normal (Step S26). In other words, the mode selection unit 6124 determines whether any malfunction has occurred in the simple development processor 6122 at Step S26.

If it is determined that the state of the third video signal is normal (Yes at Step S26), the mode selection unit 6124 shifts the signal processing apparatus 6 to the simple image output mode RmBA (Step S27). In other words, the mode selection unit 6124 outputs an instruction to select the third video signal and the setting information on the video format such as image size corresponding to the simple image output mode RmBA to the video signal output unit 6125.

After Step S27, the video signal output unit 6125 selects the third video signal from among the first, the third, and the fourth video signals, converts the selected third video signal as appropriate based on the setting information, and outputs the third video signal to the display apparatus 4 via the second transmission cable 5 (Step S28). With this processing, the display apparatus 4 displays the simple image based on the third video signal.

After Step S28, if the power is turned off while the third video signal is being output (Yes at Step S29), the signal processing apparatus 6 ends this processing.

In contrast, if the power-on state is maintained (No at Step S29), the mode selection unit 6124 determines whether the camera head 24 is being connected similarly to Steps S11, S14, and S21 (Step S30).

If it is determined that the camera head 24 is not being connected (No at Step S30), the signal processing apparatus 6 executes the output of the fourth video signal (the display of the fixed image) similarly to Step S13 (Step S31).

In contrast, if it is determined that the camera head 24 is being connected (Yes at Step S30), the signal processing apparatus 6 returns to Step S26. In other words, if the power-on state is maintained and the connected state of the camera head 24 is maintained while the third video signal is being output, the signal processing apparatus 6 monitors the state of the third video signal on a certain cycle.

If it is determined that the state of the third video signal is not normal at Step S26 (No at Step S26), the mode selection unit 6124 shifts the signal processing apparatus 6 to the fixed image output mode RmBB (Step S32). In other words, the mode selection unit 6124 outputs an instruction to select the fourth video signal and the setting information on the video format such as image size corresponding to the fixed image output mode RmBB to the video signal output unit 6125.

After Step S32, the video signal output unit 6125 selects the fourth video signal from among the first, the third, and the fourth video signals, converts the selected fourth video signal as appropriate based on the setting information, and outputs the fourth video signal to the display apparatus 4 via the second transmission cable 5 (Step S33). With this processing, the display apparatus 4 displays the fixed image based on the fourth video signal.

After Step S33, the interface module 61 outputs the certain video signal (the shutdown instruction image) similarly to Steps S8 and S23 (Step S34). With this processing, the display apparatus 4 receives input of the video signal via the second transmission cable 5 and displays the shutdown instruction image based on the video signal.

If power is turned off (Yes at Step S35), the signal processing apparatus 6 ends this processing. In contrast, if the power-on state is maintained (No at Step S35), the signal processing apparatus 6 returns to Step S34. In other words, the display of the shutdown instruction image continues until the power is turned off.

As described above, in the present embodiment, when once having switched to the abnormal mode RmB (the simple image output mode RmBA or the fixed image output mode RmBB), the signal processing apparatus 6 is unable to switch to the normal mode RmA or the maintenance mode Mm.

In the signal processing apparatus 6 according to the present embodiment described above, the operational modes (the maintenance mode Mm, the regular operational mode Rm, the normal mode RmA, the abnormal mode RmB, the simple image output mode RmBA, and the fixed image output mode RmBB) are hierarchically organized in a tree form. The signal processing apparatus 6, after the start-up of the signal processing apparatus 6, selects any operational mode from among same-level operational modes for each level from an upper level toward a lower level and switches to the operational mode. When having switched to the normal mode RmA or the abnormal mode RmB (the simple image output mode RmBA and the fixed image output mode RmBB) that have a parent-child relation with the regular operational mode Rm and are on a level therebelow, the signal processing apparatus 6 can switch to the maintenance mode Mm on an upper-level relative to the normal mode RmA and the abnormal mode RmB on condition that the signal processing apparatus 6 has again started up.

Consequently, the signal processing apparatus 6 according to the present embodiment produces an effect of making it possible to, when once having switched to the normal mode RmA or the abnormal mode RmB, avoid switching to an unintentional operational mode (the maintenance mode Mm) and to prevent image loss even when an operational error by an operator or the like occurs.

The signal processing apparatus 6 according to the present embodiment determines the state of the first video signal generated by the image processing module 63 and switches to the normal mode RmA or the abnormal mode RmB based on a determination result. After having switched to the abnormal mode RmB, the signal processing apparatus 6 determines the state of the third video signal generated by the simple development processor 6122 and switches to the simple image output mode RmBA or the fixed image output mode RmBB based on a determination result.

Consequently, even when any malfunction occurs in the image processing module 63 and/or the control module 62, the interface module 61 independently outputs the third video signal and the like, and the simple image based on the third video signal can be displayed, although the image quality thereof is inferior to the regular image based on the first video signal.

In particular, the simple development processor 6122 includes the FPGA 612 and thus has a lower possibility of a malfunction occurring than the image processing module 63, which executes software processing. Consequently, the effect of making it possible to prevent image loss can be suitably achieved.

In the signal processing apparatus 6 according to the present embodiment, the maintenance mode Mm and the regular operational mode Rm are the same-level operational modes and are the top-level operational modes among the operational modes.

In other words, the operational modes are hierarchically organized in a tree form, and the maintenance mode Mm and the regular operational mode Rm having high priority can be set on the top level, by which the signal processing apparatus 6 can switch to the maintenance mode Mm or the regular operational mode Rm having high priority quickly after the start-up of the signal processing apparatus 6. Consequently, convenience can be improved.

When having switched to maintenance mode Mm, the signal processing apparatus 6 according to the present embodiment can switch to the regular operational mode Rm on condition that the signal processing apparatus 6 has again started up.

Consequently, when once having switched to the maintenance mode Mm, the signal processing apparatus 6 can also avoid switching to an unintentional operational mode (the regular operational mode Rm) even when an operational error by an operator or the like occurs.

Other Embodiments

The embodiment for performing the present invention has been described; the present invention should not be limited by the embodiment alone.

Although the embodiment employs the endoscope 2 (a hard endoscope) using a hard scope (the insertion unit 21) as the medical observation apparatus according to the present invention, this is not limiting; a soft endoscope using a soft scope (not illustrated) may be employed. The medical observation apparatus according to the present invention is not limited to the hard endoscope and the soft endoscope and may employ an ultrasonic endoscope using a probe for ultrasonic examination or an operating microscope including an imaging element.

Although the embodiment exemplifies the six operational modes, or the maintenance mode Mm, the regular operational mode Rm, the normal mode RmA, the abnormal mode RmB, the simple image output mode RmBA, and the fixed image output mode RmBB, as the operational modes, the number of the operational modes is not limited to six and may be five or less or seven or more so long as they are hierarchically organized in a tree form.

Although the mode selection unit 6124 reads the mode shift information alone from the memory 613 at Step S3 in the embodiment, this is not limiting.

When the setting information on the video format such as image size is changed through operation on an operating unit (not illustrated) such as a mouse, a keyboard, or a touch panel during operation on the regular operational mode Rm (the normal mode RmA or the abnormal mode RmB (the simple image output mode RmBA or the fixed image output mode RmBB)), for example, the changed setting information is stored in the memory 613. At Step S3, the mode selection unit 6124 reads the setting information in addition to the mode shift information from the memory 613. By using the read setting information, an image can be displayed on a video format similar to the previous one.

Although the embodiment employs PCIe as the interface IF, PCIe is not limiting; examples that may be employed include USB, Ethernet (registered trademark), serial ATA, HDMI (registered trademark), IEEE1394 (registered trademark), DisplayPort (registered trademark), RS232C, and general purpose input/output (GPIO).

The processing procedure is not limited to the order of processing in the flowchart described in the embodiment and may be changed to the extent that no contradiction arises; the pieces of processing at Steps S20 to S24 may be performed after Step S25, for example.

REFERENCE SIGNS LIST

1 Medical observation system
2 Endoscope

3 First transmission cable
4 Display apparatus
5 Second transmission cable
6 Signal processing apparatus
7 Third transmission cable
21 Insertion unit
22 Light source apparatus
23 Light guide
24 Camera head
61 Interface module
62 Control module
63 Image processing module
64 Storage module
611 Photoelectric conversion unit
612 FPGA
613 Memory
6121 Signal conversion unit
6122 Simple development processor
6123 Fixed image generation unit
6124 Mode selection unit
6125 Video signal output unit
IF Interface
Mm Maintenance mode
Rm Regular operational mode
RmA Normal mode
RmB Abnormal mode
RmBA Simple image output mode
RmBB Fixed image output mode

The invention claimed is:

1. A signal processing apparatus that is connected to a medical observation apparatus that examines an inside of a subject and outputs an image signal responsive to an examination result and performs image processing on the image signal, the signal processing apparatus comprising:
   circuitry configured to select any operational mode from among a plurality of operational modes that include a regular operational mode in which a video signal for display is output, the operational modes being hierarchically organized in a tree form, the circuitry causing the signal processing apparatus to operate in the selected operational mode, wherein
   the operational modes include a plurality of lower-level operational modes as lower-level operational modes having a parent-child relation with the regular operational mode, and
   the circuitry is configured to
      after the signal processing apparatus has started up, select any operational mode from among same-level operational modes for each level from an upper level toward a lower level, and
      when having selected any of the lower-level operational modes, prohibit selection of an upper-level operational mode relative to the selected lower-level operational mode, and allow selection of the upper-level operational mode on condition that the signal processing apparatus has again started up.

2. The signal processing apparatus according to claim 1, further comprising a first image processor configured to perform first image processing on the image signal, wherein
   the lower-level operational modes include a normal mode in which the first image processor is caused to execute the first image processing to output a first video signal for display and an abnormal mode in which a second video signal for display different from the first video signal is output, and
   the circuitry selects the regular operational mode, then determines a state of the first video signal, and selects the normal mode or the abnormal mode based on a determination result.

3. The signal processing apparatus according to claim 2, further comprising a second image processor configured apart from the first image processor and configured to perform second image processing different from the first image processing on the image signal, wherein
   the operational modes include a simple image output mode in which the second image processor is caused to perform the second image processing to output a third video signal for display, and a fixed image output mode in which a fourth video signal for display responsive is output to a preset fixed image as lower-level operational modes having a parent-child relation with the abnormal mode, and
   the circuitry selects the abnormal mode, then determines a state of the third video signal, and selects the simple image output mode or the fixed image output mode based on a determination result.

4. The signal processing apparatus according to claim 3, wherein the second image processor includes a programmable logic device.

5. The signal processing apparatus according to claim 2, further comprising a second image processor configured apart from the first image processor and configured to perform second image processing different from the first image processing on the image signal.

6. The signal processing apparatus according to claim 5, wherein
   the operational modes include a simple image output mode in which the second image processor is caused to perform the second image processing to output a third video signal for display, and a fixed image output mode in which a fourth video signal for display responsive is output to a preset fixed image as lower-level operational modes having a parent-child relation with the abnormal mode.

7. The signal processing apparatus according to claim 6, wherein
   the circuitry selects the abnormal mode, then determines a state of the third video signal, and selects the simple image output mode or the fixed image output mode based on a determination result.

8. The signal processing apparatus according to claim 1, wherein the operational modes include a maintenance mode for maintenance of the signal processing apparatus as an operational mode on a same level as the regular operational mode.

9. The signal processing apparatus according to claim 8, wherein the regular operational mode and the maintenance mode are upper-level operational modes among the operational modes.

10. The signal processing apparatus according to claim 8, wherein when having selected the maintenance mode, the circuitry enables the regular operational mode to be selected on condition that the signal processing apparatus has again started up.

11. A medical observation system comprising:
   the signal processing apparatus according to claim 1; and
   the medical observation apparatus that examines the inside of the subject and outputs the image signal responsive to the examination result.

12. A method for a signal processing apparatus that is connected to a medical observation apparatus that examines an inside of a subject and outputs an image signal responsive to an examination result and performs image processing on the image signal, the method comprising:

selecting, by circuitry, any operational mode from among a plurality of operational modes that include a regular operational mode in which a video signal for display is output, the operational modes being hierarchically organized in a tree form;

causing, by the circuitry, the signal processing apparatus to operate in the selected operational mode, the operational modes including a plurality of lower-level operational modes as lower-level operational modes having a parent-child relation with the regular operational mode;

after the signal processing apparatus has started up, selecting any operational mode from among same-level operational modes for each level from an upper level toward a lower level; and when having selected any of the lower-level operational modes, prohibiting selection of an upper-level operational mode relative to the selected lower-level operational mode, and allowing selection of the upper-level operational mode on condition that the signal processing apparatus has again started up.

* * * * *